(12) United States Patent
Nelson et al.

(10) Patent No.: US 8,928,338 B2
(45) Date of Patent: Jan. 6, 2015

(54) SELF DIAGNOSTICS OF A PARTICULATE MATTER SENSOR

(75) Inventors: Charles S. Nelson, Fenton, MI (US);
Lary R. Hocken, Davison, MI (US);
Michael Conklin, Grand Blanc, MI (US)

(73) Assignee: Delphi Technologies, Inc., Troy, MI (US)

(*) Notice: Subject to any disclaimer, the term of this patent is extended or adjusted under 35 U.S.C. 154(b) by 926 days.

(21) Appl. No.: 12/947,867

(22) Filed: Nov. 17, 2010

(65) Prior Publication Data

US 2012/0119759 A1 May 17, 2012

(51) Int. Cl.
*G01R 27/08* (2006.01)
*G01N 35/00* (2006.01)
*F02D 41/14* (2006.01)
*G01N 15/06* (2006.01)
*F02D 41/22* (2006.01)

(52) U.S. Cl.
CPC ...... *G01N 35/00712* (2013.01); *F02D 41/1466* (2013.01); *G01N 15/0656* (2013.01); *F02D 41/222* (2013.01)
USPC .......................................... 324/691; 324/464

(58) Field of Classification Search
None
See application file for complete search history.

(56) References Cited

U.S. PATENT DOCUMENTS

| 3,656,658 | A  | * | 4/1972  | Iannetti .......................... 222/5 |
|-----------|----|---|---------|------------------------------------------|
| 4,656,832 | A  | * | 4/1987  | Yukihisa et al. ............... 60/303    |
| 4,947,125 | A  | * | 8/1990  | De Pous ......................... 324/459 |
| 6,634,210 | B1 | * | 10/2003 | Bosch et al. .................. 73/23.33  |
| 7,770,432 | B2 |   | 8/2010  | Roesch et al.                            |
| 8,230,716 | B2 | * | 7/2012  | Nelson et al. .................. 73/1.06  |
| 8,249,827 | B2 | * | 8/2012  | Nelson et al. .................. 702/183  |
| 8,707,807 | B2 | * | 4/2014  | Yadav et al. .................. 73/865.9  |
| 2008/0282769 | A1 |  | 11/2008 | Nelson                                 |
| 2008/0283398 | A1 |  | 11/2008 | Nelson et al.                          |
| 2009/0126458 | A1 |  | 5/2009  | Fleischer et al.                       |
| 2009/0139081 | A1 |  | 6/2009  | Nelson                                 |
| 2009/0314056 | A1 |  | 12/2009 | McCauley et al.                        |

* cited by examiner

*Primary Examiner* — Paresh Patel
(74) *Attorney, Agent, or Firm* — Mark H. Svoboda

(57) ABSTRACT

A particulate matter sensor includes first and second electrodes spaced from each other with a bias resistor connected between the first and second electrodes. The particulate matter sensor allows an open circuit fault condition in the sensor or in the connectors or wiring to the sensor to be detected. A sensing system using the particulate matter sensor and a method for diagnosing faults in a sensing system are also provided.

9 Claims, 3 Drawing Sheets

US 8,928,338 B2

SELF DIAGNOSTICS OF A PARTICULATE MATTER SENSOR

FIELD OF THE INVENTION

This application relates to particulate matter sensing systems and methods and apparatus for diagnosing particulate matter sensing systems.

BACKGROUND

Soot sensors, also known as particulate matter (PM) sensors, are often used in vehicles having diesel engines. A particulate matter sensor may be located upstream from a particulate filter, where the sensor is exposed to exhaust flow from the engine having soot particles entrained in the exhaust gas. Alternatively, a particulate matter sensor may be located in a gas stream downstream from a particulate filter, where the sensor is used to monitor the proper operation of the particulate filter.

A known method of sensing soot uses a particulate matter sensor having two electrodes that are spaced from one another. In the absence of soot, there is very low electrical conductivity between the electrodes. As soot accumulates on the surface of the sensor, soot particles act to bridge the gap between the electrodes. Because the soot particles are electrically conductive, the conductivity between the electrodes increases, and this change in conductivity can be related to the amount of soot in the gas stream. Sensors that operate according to this principle are disclosed in U.S. patent application Ser. No. 11/749,262 published as US Patent Application Publication 2008/0283398, U.S. patent application Ser. No. 11/750,883 published as US Patent Application Publication 2008/0282769, and U.S. patent application Ser. No. 11/998, 238 published as US Patent Application Publication 2009/0139081, the contents of all of which are hereby incorporated by reference in their entirety.

Government regulations require that the particulate matter sensor have self diagnostics (i.e. On Board Diagnostics or OBD) capability to verify that it is functioning properly. However, with a normally open circuit device, and soot normally not present, this can be difficult. The sensor must be able to verify that the circuit is functioning properly and that if a conductive material lands on the electrode, the sensor can detect it. In a conventional sensor as described, a "clean" sensor, that is a sensor with no accumulated soot, will appear electrically as an open circuit. The same open circuit indication may result from a damaged sensor or a disconnected wiring harness.

Accordingly, the inventors herein have recognized a need for an improved sensing system having a particulate matter sensor that reduces and/or eliminates the foregoing deficiencies.

SUMMARY OF THE INVENTION

A particulate matter sensor in accordance with an aspect of the invention is provided. The particulate matter sensor includes a bias resistor electrically connected between the sensing electrodes to provide a baseline condition having non-zero conductivity (non-infinite resistance). The bias resistor on the particulate matter sensor allows a controller connected to the particulate matter sensor to discriminate between a properly connected particulate matter sensor and an open circuit condition due to a wiring fault or a damaged sensor.

A method for diagnosing a soot sensing system according to a further aspect of the invention is provided. The method includes sensing an electrical property of a particulate matter sensor, comparing the electrical property to predetermined threshold values, and determining if a fault condition exists based on the results of the comparison.

DETAILED DESCRIPTION OF DRAWINGS

At the outset of the description, it should be noted that the terms "first," "second," and the like, herein do not denote any order, quantity, or importance, but rather are used to distinguish one element from another, and the terms "a" and "an" herein do not denote a limitation of quantity, but rather denote the presence of at least one of the referenced items. The modifier "about" used in connection with a quantity is inclusive of the stated value and has the meaning dictated by the context (e.g., includes the degree of error associated with measurement of the particular quantity). It is noted that the terms "left", "right", "horizontal", "vertical", "bottom", and "top" are used herein, unless otherwise noted, merely for convenience of description, and are not limited to any one position or spatial orientation. Finally, unless defined otherwise, technical and scientific terms used herein have the same meaning as is commonly understood by one of skill in the art to which this invention belongs.

Figure 1:
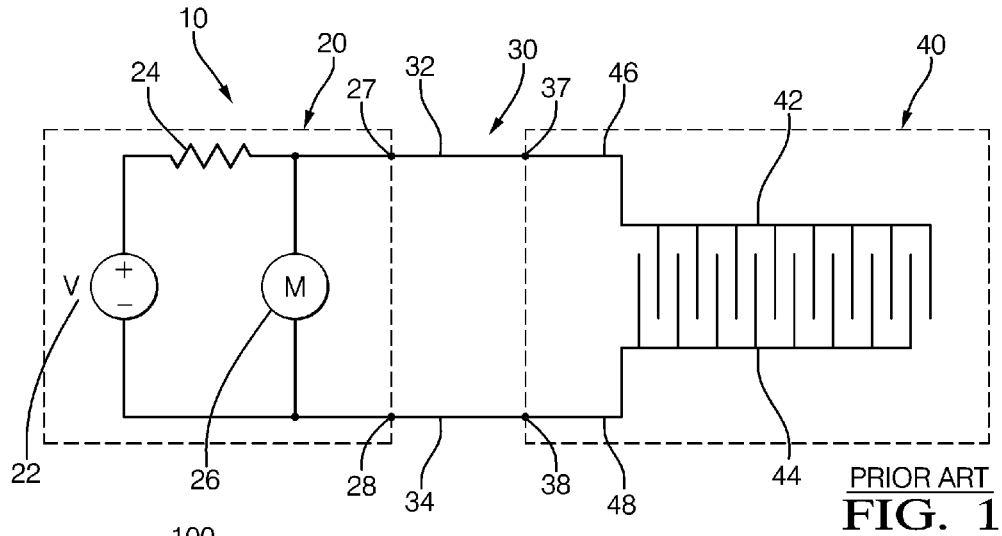
FIG. 1 is an electrical schematic of a prior art particulate matter sensing system.

FIG. 1 is an electrical schematic of a prior art particulate matter sensing system 10. The system may be generally considered as partitioned as indicated into a controller portion 20, a wiring harness portion 30, and a sensing element portion 40. The controller portion 20 comprises a means for measuring the impedance of a circuit connected thereto. In the exemplary controller portion 20 in FIG. 1, the impedance measurement means includes a voltage source 22 that provides a voltage value $V_{supply}$, a pull-up resistor 24 having a resistance value $R_{pullup}$, and a voltage measurement means 26. While voltage source 22 is depicted in FIG. 1 as a DC source with a given polarity, it will be appreciated that voltage source 22 can alternatively be an AC source, a DC source having opposite polarity from what is depicted, or a source providing both an AC and a DC voltage component, without departing from the inventive concept described herein. The controller portion 20 electrically interfaces to the wiring harness portion 30 by connection means 27 and 28. The wiring harness portion 30 includes conductors 32 and 34. The wiring harness portion 30 electrically interfaces to the sensing element portion 40 by connection means 37 and 38. The sensing element portion 40 includes a first electrode 42 electrically connected by conductor 46 to connection means 37, and a second electrode 44 electrically connected by conductor 48 to connection means 38.

As formed on the sensing element, the first electrode 42 is electrically isolated from the second electrode 44, so that a sensing element 40 in the absence of particulate matter appears electrically as an open circuit when measured between connection means 37 and connection means 38. In the absence of particulate matter, the voltage measured by measurement means 26 will be essentially equal to $V_{supply}$, the voltage provided by voltage source 22.

The first electrode 42 and second electrode 44 are preferably shaped in the form of interdigitized fingers with a small gap therebetween. In operation, particulate matter that is deposited on the sensing element so as to bridge the gap between the electrodes 42, 44 can be detected because the particulate matter forms a resistive path bridging the normally open circuit between the electrodes 42, 44. If the resistance of the particulate matter bridging the electrodes is assigned the value $R_{particulate}$, the voltage measured by measurement means 26 will be:

$$V_{measured} = V_{supply} \frac{R_{particulate}}{R_{pullup} + R_{particulate}}$$

As particulate matter accumulates between first electrode 42 and second electrode 44, the resistance $R_{particulate}$ will decrease, and the voltage $V_{measured}$ at measurement means 26 will decrease from the maximum value of $V_{supply}$. The controller portion can thereby determine the impedance connected across connection means 27 and 28 as a function of the voltage measured between points 27 and 28.

While the prior art arrangement shown in FIG. 1 can effectively sense particulate matter, it is not well suited for providing diagnostics of a particulate matter sensing system. As described earlier, a sensing element 40 absent of particulate matter, which is a normal condition for an installed sensing system, will electrically appear to the controller 20 as an open circuit. Several fault conditions may occur that would also appear as an open circuit. For example, an electrical connector such as connection means 27, 28, 37, or 38 may become disconnected. A wire 32, 34 in wiring harness portion 30 may break. Damage may occur to sensing element portion 40 resulting in a break in conductor 46 or 48. None of these fault conditions can be detected in prior art system 10, as any of these fault conditions will result in a measured voltage $V_{measured}$ at measurement means 26 equal to the supply voltage $V_{supply}$, which is the same voltage that will be present for a properly connected and operating sensing element in the absence of particulate matter.

Figure 2:
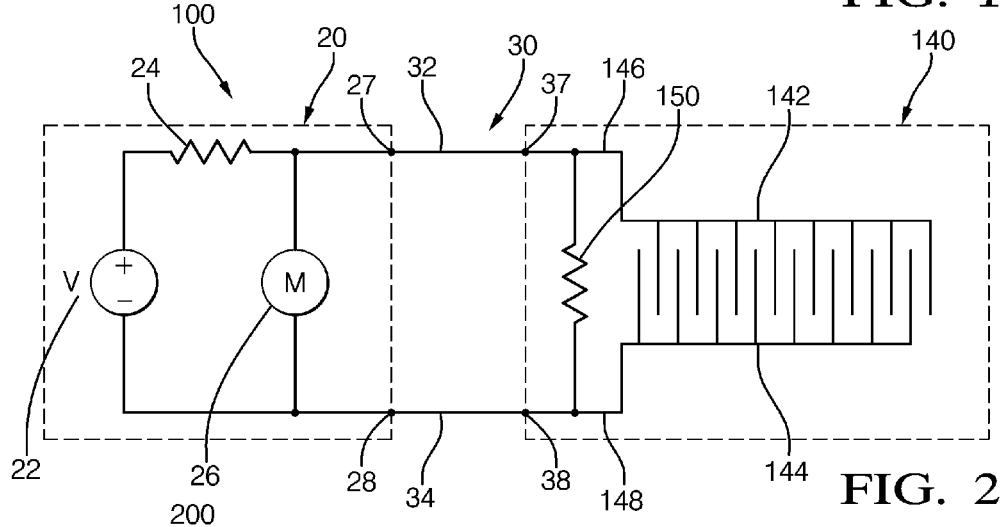
FIG. 2 is an electrical schematic of a particulate matter sensing system according to an exemplary embodiment of the invention.

FIG. 2 is an electrical schematic of a particulate matter sensing system 100 according to an aspect of the present invention. Controller portion 20 and wiring harness portion 30 are essentially the same as in the prior art system 10. The sensing element portion 140 includes a first electrode 142 electrically connected by conductor 146 to connection means 37, and a second electrode 144 electrically connected by conductor 148 to connection means 38. The sensing element portion 140 in FIG. 2 contains an additional bias resistor 150 having a resistance value of $R_{bias}$ electrically connected between conductors 146 and 148. The resistance of the sensing element $R_{sensor}$ as measured between connection means 37 and connection means 38 is the parallel combination of $R_{bias}$ and the resistance resulting from particulate matter bridging the gap between the first electrode 142 and the second electrode 144. $R_{sensor}$ can be represented mathematically as:

$$R_{sensor} = \frac{R_{bias} \times R_{particulate}}{R_{bias} + R_{particulate}}$$

In the absence of particulate matter on sensing element 140, the term $R_{particulate}$ is very large compared to $R_{bias}$, and the effective sensor resistance $R_{sensor}$ is essentially equal to $R_{bias}$. This condition provides the maximum resistance value of $R_{sensor}$. As particulate matter accumulates so as to bridge the gap between the first electrode 142 and the second electrode 144, the effective sensor resistance $R_{sensor}$ will decrease from its maximum value of $R_{bias}$.

It will be appreciated that for a circuit having two resistances in parallel, the effective resistance of the parallel combination will be less than the resistance of the smaller of the two resistances. If there is a large difference in the magnitudes of the two resistances, the smaller resistance will dominate the value of the parallel combination. For this reason, it is desirable to set the value of $R_{bias}$ as high as is practicable, so that the parallel combination is sensitive to resistance change caused by the accumulation of particulate matter between the first electrode 142 and the second electrode 144. Since the resistance value of particulate matter is high, Rbias should be greater than 100 kilohms, with a value greater than 1 megohm preferred, and a value about 10 megohms more preferred.

For the particulate matter sensing system 100 depicted in FIG. 2, the voltage measured by measurement means 26 will be:

$$V_{measured} = V_{supply} \frac{R_{sensor}}{R_{pullup} + R_{sensor}}$$

In the absence of particulate matter, the value of $R_{sensor}$ will be at its maximum and will essentially equal $R_{bias}$. Under this condition, the voltage measured by measurement means 26 will be:

$$V_{measured} = V_{supply} \frac{R_{bias}}{R_{pullup} + R_{bias}}$$

This value represents the highest voltage that should be present in a properly connected, undamaged particulate matter sensing system 100. For an exemplary embodiment with $R_{bias}$ equal to 10 megohms and $R_{pullup}$ equal to 1 megohm, the voltage measured by measurement means 26 with a sensing element 140 absent particulate matter would be about 91 percent of the supply voltage $V_{supply}$. A voltage below this level would be indicative of accumulating particulate matter between the first electrode 142 and the second electrode 144.

As indicated earlier, several fault conditions may occur in a particulate matter sensing system that would appear as an open circuit. For example, an electrical connector such as connection means 27, 28, 37, or 38 may become disconnected. A wire 32, 34 in wiring harness portion 30 may break. Damage may occur to sensing element portion 140 resulting in a break in conductor 146 or 148 between connection means 37, 38 and bias resistor 150. Any of these fault conditions would result in a voltage measured by measuring means of essentially $V_{supply}$, which is higher than the highest voltage that would be present in a properly connected system (for example 91% of Vsupply with $R_{pullup}$=1 megohm and $R_{bias}$=10 megohms). A voltage in excess of the maximum voltage expected from a properly connected undamaged sensor can be used to indicate the presence of a fault condition. It will be appreciated that the exemplary particulate matter sensing system 100 as shown in FIG. 2 provides improved diagnostic capability over the prior art system of FIG. 1.

The inventors of the present invention have recognized that further improvement can be made to the system depicted in FIG. 2. For example, if sensing element 140 was damaged such that an open circuit occurred at first electrode 142, at second electrode 144, or in a portion of conductor 146 or 148 to the right of the junction of resistor 150 to either of these conductors, that damage would not be recognizable as an abnormal voltage measurement at measurement means 26.

Figure 3:
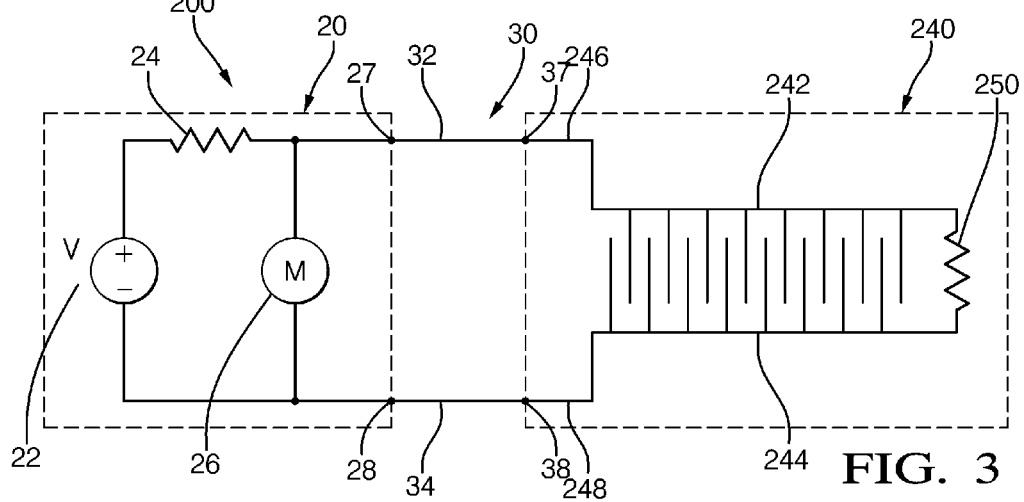
FIG. 3 is an electrical schematic of a particulate matter sensing system according to an alternate exemplary embodiment of the invention.

FIG. 3 is an electrical schematic diagram of an alternate embodiment that provides certain advantages over the embodiment in FIG. 2. In FIG. 3, controller portion 20 and wiring harness portion 30 are substantially as described in relation to FIGS. 1 and 2. Sensing element portion 240 includes a first conductor 246 electrically connected to first electrode 242 and a second conductor 248 electrically connected to second electrode 244. Sensing element portion 240 also includes a bias resistor 250 located such that first electrode 242 is electrically connected between connection means 37 and a first end of bias resistor 250, and second electrode 244 is electrically connected between electrical connection means 39 and a second end of bias resistor 250.

Operation of particulate matter sensing system 200 including sensing element portion 240 can be understood using the same description and equations used to describe the operation of particulate matter sensing system 100 in FIG. 2 as previously described. Relocating the bias resistor 250 so that the first and second electrodes 242 and 244 are electrically between the connection means 37, 39 and the bias resistor 250 allows improved diagnostic capability. As described earlier, the system 100 depicted in FIG. 2 does not permit detection of damage to any part of the sensing element 140 to the right of the junctions of bias resistor 150 with conductors 146 and 148. In contrast, the location of bias resistor 250 in FIG. 3 permits recognition of an open circuit fault anywhere on the sensing element 240, in addition to allowing detection of fault conditions associated with connection means 27, 28, 37, or 38, as well as open circuit faults in wires 32, 34.

Figure 4:
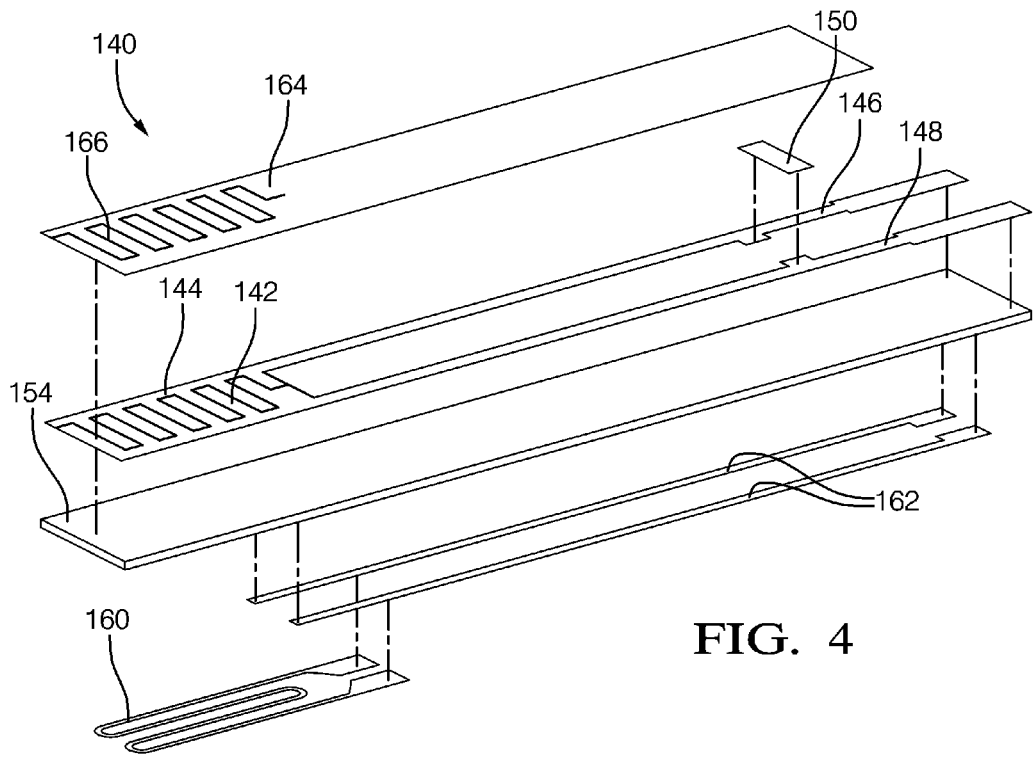
FIG. 4 is an exploded perspective view of a sensing element according to an exemplary embodiment of the invention.

FIG. 4 is an exploded perspective view of a sensing element 140 according to an aspect of the invention. The sensing element 140 includes an electrically insulating substrate 154. While shown as a single layer, it will be appreciated that substrate 154 may be formed by laminating together a plurality of layers. Conductive material disposed on one surface of substrate 154 is patterned to form conductors 146 and 148 and electrodes 142 and 144. Resistor material to form bias resistor 150 is deposited so as to connect to conductors 146 and 148.

A particulate matter sensor may also include a heating means that is controllable to raise the temperature in the vicinity of the electrodes 142, 144 on the sensing element. Raising the temperature sufficiently will result in the particulate matter being removed from the surface of the sensing element, thereby restoring the resistance of the area between the sensing electrodes 142, 144 to a high resistance or essentially open circuit condition. This open circuit condition appears electrically in parallel with the bias resistor 150, so that the total resistance measured between connection means 37 and connection means 38 is restored to $R_{bias}$. The sensing element 140 depicted in FIG. 4 includes a heater 160 and heater leads 162, on the opposite surface of the substrate from the electrodes 142, 144. The heater 160 is positioned to allow the heater 160 to clean the particulate matter from the vicinity of the electrodes 142, 144 when the heater 160 is electrically powered by supplying current through heater leads 162.

A protective layer 164 may also be included to protect the conductive material that forms electrodes 142 and 144, as well as portions of the conductors 146, 148 that may be exposed to abrasive particles in the gas stream being measured. The protective layer 164 includes an open area 166 exposing the gap between the electrodes 142 and 144 to allow particulate matter to bridge the electrodes 142 and 144. The protective layer 164 may also extend to cover bias resistor 150.

To facilitate interchangeability of sensing elements 140, 240 with controllers 20, it is desired to manufacture each sensing element 140, 240 so that the bias resistor 150, 250 has a known predetermined resistance value. This is achieved by depositing the bias resistor on the substrate to a resistance value lower than the final desired resistance value, then using an ablative trimming method such as laser trimming to increase the resistance to the target value, using known trimming techniques.

Figure 7:
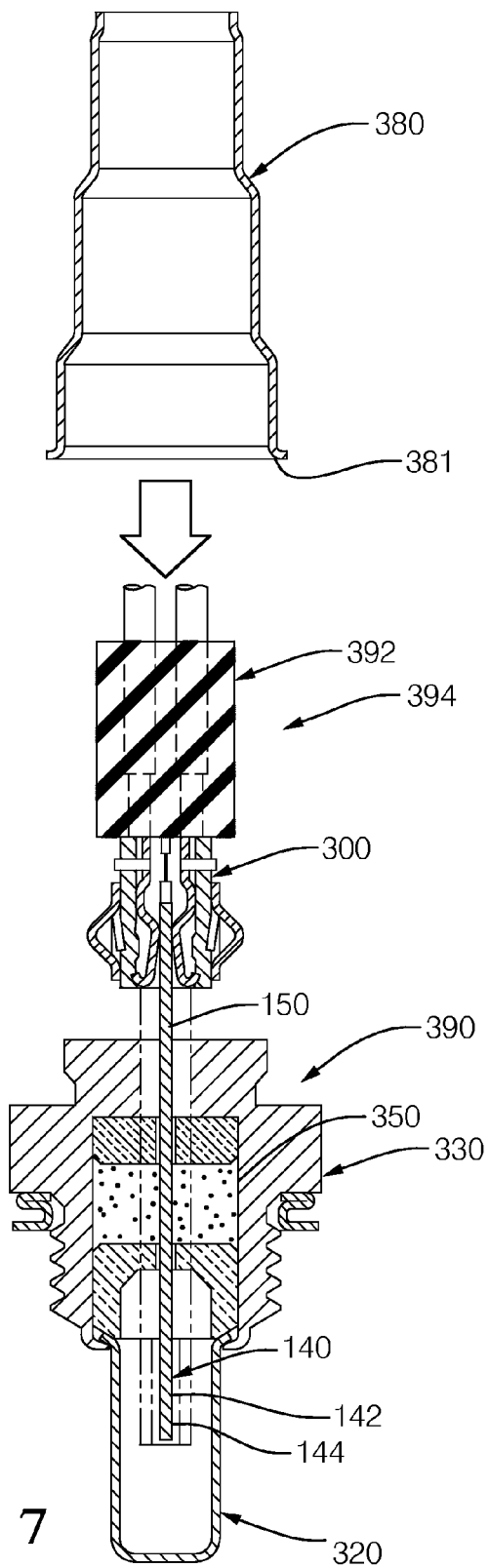
FIG. 7 is a schematic cross-sectional view illustrating components of a sealed sensor assembly incorporating a sensing element according to an embodiment of the invention.

It is desirable to include a sealing means in the mounting arrangement for the sensing element so that a first portion of the sensing element that includes the electrodes is exposed to the gas stream being measured, and a second portion of the sensing element that includes the connection means 37, 38 to the sensing element is sealed from exposure to the gas stream. A suitable mounting arrangement for the sensing element 140, 240 is an arrangement as disclosed in US patent application Ser. No. 12/143,505 published as US Patent Application Publication 2009/0314056, the disclosure of which is hereby incorporated by reference in its entirety. As shown in FIG. 7, an exemplary embodiment of gas sensor includes a generally cylindrical lower shield 320, sensor shell 330, flat-plate ceramic sensor 140, sensor packing 350, upper shield 380 and electrical connector assembly 300. The lower shield 320, sensor shell 330, gas sensor 140 and packing 350 may be assembled to form a sensor subassembly 390. The electrical connector 300 is inserted onto the sensor subassembly 390 by insertion of the upper end of sensor 140 into a sensor pocket on the insertion end of electrical connector 300, as shown in FIG. 7, to form a sensor/connector subassembly 392. A gas-tight sealed joint between the inner surface of the upper shield 380 and the outer surface of the sensor shell 330 may be formed by placing the open end 381 of the upper shield 380 over the sensor shell 330 and crimping to plastically deform the upper shield 380 over the sensor shell 330. It is desirable to position the bias resistor 150, 250 on the side of the sealing means that is protected from the gas stream. Additionally, it is appreciated it is desirable to minimize the temperature extremes experienced by the bias resistor 150, 250 in use. For this reason, it is preferred that the resistor 150, 250 is located on a portion of the substrate 154 that is remote from the portion of the substrate 154 that is heated by heater 160.

Figure 5:
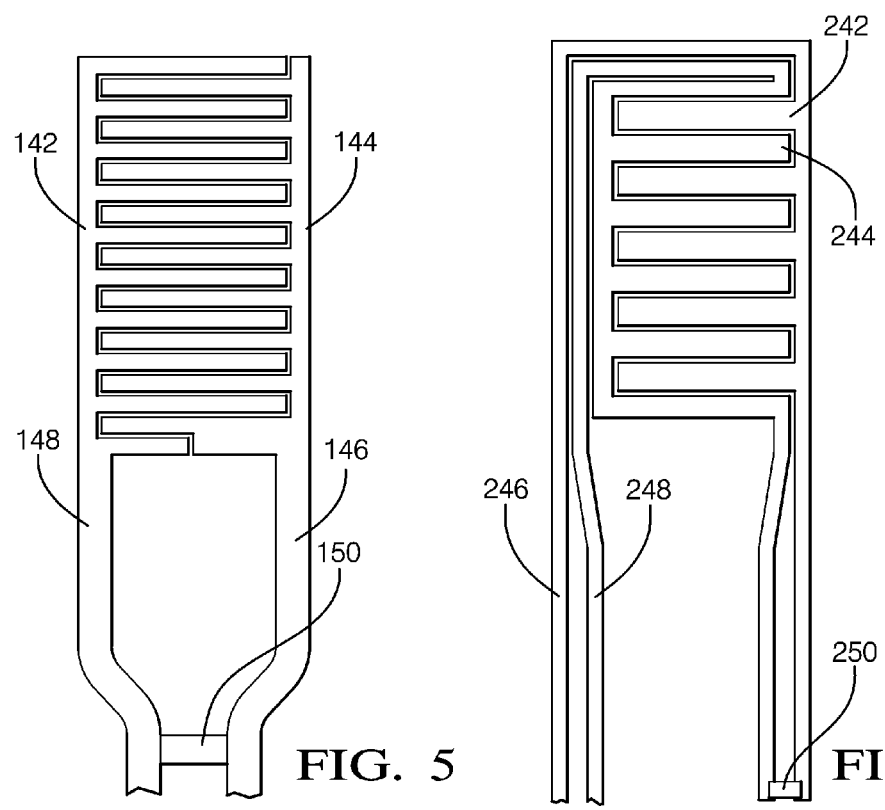
FIG. 5 is a plan view of a sensing element according to an exemplary embodiment of the invention

FIG. 5 is a plan view of the conductor and resistor pattern of a sensing element 140 as depicted in FIGS. 2 and 4. Bias resistor 150 is located remote from the first electrode 142 and the second electrode 144 to minimize heating of the bias resistor 150 when the heater (not shown) is activated to clean the particulate matter from the vicinity of the electrodes 142, 144, as well as to facilitate locating the bias resistor 150 on the side of the sealing means that will protect the bias resistor 150 from the gas stream.

Figure 6:
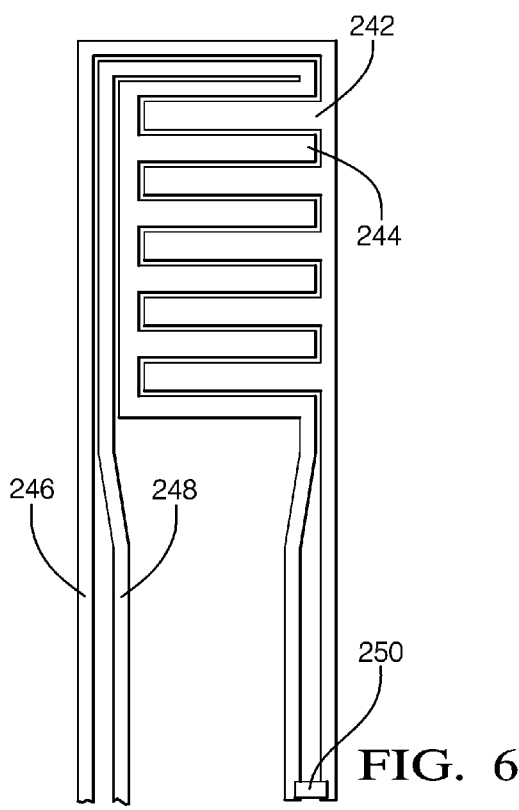
FIG. 6 is a plan view of a sensing element according to an alternate exemplary embodiment of the invention.

FIG. 6 is a plan view of the conductor and resistor pattern of a sensing element 240 as described and depicted by FIG. 3. The bias resistor 250 is connected such that the first electrode 242 is electrically in series between bias resistor 250 and conductor 246, and the second electrode 244 is electrically in series between bias resistor 250 and conductor 248. The pattern shown in FIG. 6 allows detection of an open circuit fault anywhere in the particulate sensing system 200, including an open circuit condition in the conductive material that forms electrodes 242 and 244 on sensing element 240. Additionally, the pattern shown in FIG. 6 allows the bias resistor 250 to be located remote from the first electrode 242 and the second electrode 244, to minimize heating of the bias resistor 250 when the heater (not shown) is activated to clean the particulate matter from the vicinity of the electrodes 242, 244, as well as to facilitate locating the bias resistor 250 on the side of the sealing means that will protect the bias resistor 250 from the gas stream.

It will be appreciated that the impedance indicated by a properly connected, undamaged particulate matter sensor according to aspects of this invention will have a maximum value equal to the resistance value of the bias resistor, in the absence of particulate matter on the sensor. As particulate matter accumulates on the sensor, the impedance will decrease from this maximum value. If an impedance greater than the resistance of the bias resistor is detected, this is an indication of a fault condition such as a disconnected electrical connector, a broken wire, or a damaged sensor. In response to detection of a fault condition, appropriate action may be taken, for example, an indicator light may be actuated and/or an operating parameter of the engine or exhaust system may be adjusted.

While the embodiments of a particulate matter sensing system that facilitate diagnosis of fault conditions have been shown and described in detail, it is to be understood that the subject matter which is encompassed by the present invention is limited only by the following claims.

The invention claim is:

1. A sensor for detecting particulate matter in a gas stream, comprising:
    an electrically nonconductive substrate;
    a first electrode disposed on a first surface of the substrate;
    a second electrode disposed on the first surface of the substrate and spaced away from the first electrode;
    a bias resistor disposed on the substrate electrically connected between the first electrode and the second electrode; and
    a sealing means to seal a portion of the substrate from the gas stream, wherein the bias resistor is located on the portion of the substrate that is sealed from the gas stream.

2. The sensor of claim 1, additionally comprising a heater means disposed to heat a first portion of the substrate, wherein the bias resistor is located on a second portion of the substrate remote from the heater means.

3. The sensor of claim 1 wherein the bias resistor has a resistance value greater than about 100 kilohms.

4. The sensor of claim 3 wherein the bias resistor has a resistance value greater than about 1 megohm.

5. The sensor of claim 4 wherein the bias resistor has a resistance value of about 7 megohms to 10 megohms 6. The sensor of claim 4 wherein the bias resistor has a resistance value greater than about 10 megohms.

7. The sensor of claim 1 additionally comprising first connection means electrically connected to the first electrode and second connection means electrically connected to the second electrode, said first and second connection means adapted to connect to an impedance measurement means external to the sensor, wherein the first electrode is disposed electrically in series between the first connection means and the bias resistor.

8. The sensor of claim 1 wherein the bias resistor is formed by depositing a film of resistive material on the substrate and is subsequently trimmed by ablative means to increase its resistance value to a predetermined target resistance value.

9. A method for diagnosing a particulate matter sensing system, said system comprising an electronic controller portion, an electrical connection means connected to the controller portion, and a sensing element connected to the electrical connection means, said sensing element comprising two electrodes spaced from one another and a bias resistor connected electrically between the two electrodes; said method comprising the steps of:
    determining the impedance of the combined electrical connection means and sensing element, and
    indicating a fault condition if the impedance of the combined electrical connection means and sensing element is greater than the resistance value of the bias resistor.

* * * * *